United States Patent
Gu et al.

(10) Patent No.: US 10,435,384 B2
(45) Date of Patent: Oct. 8, 2019

(54) **METHOD FOR EXTRACTING HERBACETIN FROM PLANTS OF *RHODIOLA* L**

(71) Applicant: TAIZHOU DANDING BIOTECHNOLOGY CO., LTD., Taizhou, Jiangsu (CN)

(72) Inventors: Zhengbing Gu, Jiangsu (CN); Jie Zhang, Jiangsu (CN); Yuehong Tao, Jiangsu (CN); Cheng Zeng, Jiangsu (CN); Lili Xu, Jiangsu (CN)

(73) Assignee: TAIZHOU DANDING BIOTECHNOLOGY CO., LTD., Taizhou (CN)

( * ) Notice: Subject to any disclaimer, the term of this patent is extended or adjusted under 35 U.S.C. 154(b) by 0 days.

(21) Appl. No.: 16/104,951

(22) Filed: Aug. 20, 2018

(65) Prior Publication Data

US 2018/0354926 A1 Dec. 13, 2018

Related U.S. Application Data

(63) Continuation of application No. PCT/CN2016/074095, filed on Feb. 19, 2016.

(51) Int. Cl.
   *C07D 311/30* (2006.01)
   *A61K 31/352* (2006.01)
   *A61K 36/41* (2006.01)

(52) U.S. Cl.
   CPC .......... *C07D 311/30* (2013.01); *A61K 31/352* (2013.01); *A61K 36/41* (2013.01); *A61K 2236/00* (2013.01)

(58) Field of Classification Search
   CPC .... C07D 311/30; A61K 31/352; A61K 36/41; A61K 2236/00
   See application file for complete search history.

(56) References Cited

PUBLICATIONS

International Search Report of PCT Patent Application No. PCT/CN2016/074095 dated Nov. 25, 2016.
Tao Li et al., Study on the Chemical Constituents of *Rhodiola crenulata*, West China Journal of Pharmaceutical Sciences, Apr. 30, 2012, pp. 367-370, vol. 27, No. 4.
Chinese Pharmacopoeia, Edition 2015, pp. 154-155.

*Primary Examiner* — Timothy R Rozof

(57) ABSTRACT

A method for extracting herbacetin from plants of *Rhodiola* L., comprising the following steps: 1) performing an extracting process for the pulverized medical *Rhodiola* L. with an extracting solvent, and condensing to obtain an extract; 2) performing a leaching process for the extract and performing an acid hydrolysis for the extracted aqueous layer; 3) performing a leaching process for the solution after the acid hydrolysis with an organic solvent, combining the organic layer and concentrating under reduced pressure to obtain a herbacetin extract; 4) treating the herbacetin extract through polyamide column chromatography, collecting the outflow containing herbacetin and drying through condensation to obtain a crude herbacetin product; 5) treating the crude herbacetin product through reverse-phase silica-gel column chromatography, collecting the outflow containing herbacetin, drying through condensation and recrystallizing to obtain a pure herbacetin product. The invention for herbacetin preparation is characterized by simple process, high yield.

12 Claims, 3 Drawing Sheets

|   | Retention time (min) | Area (μV*s) | Height (μV) | Area (%) | Integral type |
|---|---|---|---|---|---|
| 1 | 13.200 | 10938 | 889 | 0.85 | BB |
| 2 | 17.781 | 1269561 | 96186 | 99.15 | BB |

METHOD FOR EXTRACTING HERBACETIN FROM PLANTS OF *RHODIOLA* L

CROSS-REFERENCE TO RELATED APPLICATIONS

This application is a continuation application of International Patent Application No. PCT/CN2016/074095 filed on Feb. 19, 2016, the entire contents of which are incorporated herein by reference.

TECHNICAL FIELD

The invention, belonging to the field of pharmaceutical chemistry, relates to the separation and extraction method for compounds in chemical field, in particular to a method for extracting herbacetin from plants of *Rhodiola* L.

BACKGROUND

Plants of *Rhodiola* L. of Crassulaceae are perennial herbaceous or subshrub plants. There are about 90 species of such plants in the world, in which 73 species exist in China. For the study of various plants of *Rhodiola* L., domestic and foreign scholars mainly focus on more than ten species such as *Rhodiola crenulata, Rhodiola rosea, Rhodiola dumulosa, Rhodiola sachalinensis, Rhodiola kirilowii* and *Rhodiola sacra*. Various species of *Rhodiola* L. have great difference in chemical compositions and efficacy. The plant of *Rhodiola* L. recorded in *Chinese Pharmacopoeia* (Edition 2015) refers to the dry radix and rhizome of *Rhodiola crenulata*, a plant of Crassulaceae which is featured by sweet and bitter taste. It can affect the lung meridian and the heart meridian, and has the effects of benefiting qi for activating blood circulation, dredging arteries and relieving asthma for diseases with qi deficiency and blood stasis, chest stuffiness and pains, hemiplegia and listlessness and asthma. Due to its anti-fatigue effect superior to ginseng and acanthopanax root, and its exciting intellectual activity efficacy superior to acanthopanax root, it is often taken as a good nutrition medicine by people to eliminate fatigue and withstand coldness.

Modern medicine indicates that the main effective components of *Rhodiola* L. are flavonoids, tyrosol and its glycosides. The flavonoids mainly include herbacetin and its corresponding glycosides. Herbacetin can effectively eliminate DPPH free radicals and hydroxyl radicals and inhibit protein oxidation, and its antioxidant activity is stronger than other glycosides. Researches show that the pharmacological activity decreases after the glycosylation of the $7^{th}$ hydroxyl group of ring A in the structure of herbacetin. The more sugar content exists, the lower the activity is. The antioxidant activity of flavonoids compounds increases with the phenolic hydroxyl groups in the molecule. In addition, herbacetin can induce the apoptosis of human hepatocellular carcinoma cell HepG2 and has a potential to be developed into a new anti-cancer preparation.

Herbacetin refers to 3,4',5,7,8-pentahydroxyflavone, which mainly exists in the plants of Crassulaceae. Researches indicate that *Rhodiola* L. has very low content of free herbacetin. Upon analysis on 12 different sources of medical *Rhodiola* L. (including the control *Rhodiola crenulata* with batch No. 121412-200902 and *Rhodiola sachalinensis* with batch No. 121657-201101 provided by National Institutes for Food and Drug Control, NIFDC)), it is found that the content of free herbacetin in them is only 0.0022%-0.061%. See Table 1 for specific data.

TABLE 1

Free herbacetin content in rhodiola rosea from 12 different sources

| Sample No. | Source | Herbacetin content |
|---|---|---|
| 1 | Nyingchi Prefecture in Tibet Autonomous Region | 0.00416% |
| 2 | Shannan prefecture in Tibet Autonomous Region | 0.00496% |
| 3 | Lijiang Houshan Area of Yunnan | 0.00432% |
| 4 | Changbai Mountain of Jilin | 0.00232% |
| 5 | Tibet No. 1 | 0.00710% |
| 6 | Tibet No. 2 | 0.0129% |
| 7 | Tibet No. 3 | 0.0109% |
| 8 | Tibet No. 4 | 0.00580% |
| 9 | Tibet No. 5 | 0.0607% |
| 10 | Tibet No. 6 | 0.00699% |
| 11 | *Rhodiola crenulata* from NIFDC | 0.0223% |
| 12 | *Rhodiola sachalinensis* from NIFDC | 0.00409% |

The process for direct separation of free herbacetin from medical *Rhodiola* L. has high difficulty and low yield, and it is not suitable for industrial production and is difficult to meet the needs of scientific research and new drug research and development, thus seriously limiting its in-depth research. However, the content of glycosides (e.g., herbacetin-7-0-rhamnoside and herbacetin-7-0-(3"-β-D-glucosyl)-rhamnoside) with herbacetin as aglycone is relatively high in the plants of *Rhodiola* L.

At present, few research reports on herbacetin are available, and no process route is disclosed so far suitable for the industrial production and preparation of high-purity herbacetin.

SUMMARY OF THE INVENTION

The invention is to prepare herbacetin by taking medical *Rhodiola* L. as raw material and using acid hydrolysis, polyamide column chromatography and reverse-phase silica-gel column chromatography as operation processes. Due to simple process, high yield (in Table 1, the content of free herbacetin in medical *Rhodiola crenulata* of Tibet No. 5 is only 0.06%, but the content of herbacetin in hydrolysate after acid hydrolysis is up to 4.36%, which increases by 72 times) and strong specificity, such method is suitable for the industrial production and can provide a solid material basis for testing pharmacological activities of *Rhodiola* L. such as antioxidation, treatment of cardiovascular and cerebrovascular diseases and antitumor effect.

The method for extracting herbacetin from plants of *Rhodiola* L. of the invention comprises the following steps:

1) performing an extracting process for the pulverized medical *Rhodiola* L. with an extracting solvent, and condensing the solution under reduced pressure to obtain an extract;

2) performing a leaching process for the extract and performing an acid hydrolysis for the leached aqueous layer;

3) performing a leaching process for the solution after the acid hydrolysis with an organic solvent, concentrating the organic layer under reduced pressure to obtain a herbacetin extract;

4) treating the herbacetin extract through polyamide column chromatography, collecting the outflow containing herbacetin and drying through condensation to obtain a crude herbacetin product;

5) treating the crude herbacetin product through reverse-phase silica-gel column chromatography, collecting the outflow containing herbacetin, drying through condensation and recrystallizing to obtain a pure herbacetin product.

In order to solve the above problems, the *Rhodiola* L. in step 1) is any one of plants of *Rhodiola* L. in Crassulaceae, containing herbacetin-7-0-rhamnoside and herbacetin-7-0-(3"-β-D-glucosyl)-rhamnoside, with the total content of not less than 0.08%.

The extracting solvent in step 1) is a methanol-aqueous solution with the mass percent of 30.0%-99.9% or an ethanol-aqueous solution with the mass percent of 70.0%-90.0%.

The extracting process in step 1) comprises any one of immersion, percolation, ultrasonic and heating reflux methods.

The leaching process in step 2) is performed by using petroleum ether with a boiling range from 60° C. to 90° C., and the ratio of the dosage of petroleum ether to that of the extract is (1-3):1 (v/v). The acid hydrolysis in step 2) refers to a direct acid hydrolysis or a two-phase acid hydrolysis performed by using any one of hydrochloric acid, sulfuric acid and formic acid, with the mass percentage of 0.2%-10.0%.

The organic phase in the two-phase acid hydrolysis comprises any one of petroleum ether-ethyl acetate (1:1) (v/v), methylbenzene and ethyl acetate.

The heating reflux temperature is 50° C.-100° C. and the acid hydrolysis time is 0.5 h-12.0 h during the acid hydrolysis in step 2).

The organic solvent for the leaching process in step 3) is petroleum ether-ethyl acetate (1:1) (v/v) or ethyl acetate, the ratio of the organic solvent to the solution of acid hydrolysis is (1:3):1 (v/v) each time, and the leaching process is performed for 3-5 times.

The elution condition for polyamide column chromatography in step 4) is based on the ratio of petroleum ether to ethyl acetate (1:1) (v/v).

The reverse-phase silica-gel column chromatography in step 5) is performed by using a C18 reverse-phase column, and the pre-packed column with an inner diameter of 50 mm or the pre-packed column with an inner diameter of 100 mm or the DAC preparative column is used as the C18 reverse-phase column.

The eluent for reverse-phase silica-gel column chromatography in step 5) is an aqueous acetonitrile solution or an aqueous methanol solution, and the recrystallizing process is performed by using a methanol solution.

The invention has the following beneficial effects:

1) The invention can be used to prepare high-purity herbacetin with a purity of 90.0%-99.9%;

2) The invention can be used to obtain herbacetin of gram grade or kilogram grade so as to meet the requirements of industrial production;

3) Compared with the disadvantages of complex process, high cost and long purification cycle when herbacetin is prepared by using glycoside monomer component (with herbacetin as aglycone) as raw material, the invention has the advantages of simple process, easy operation, economical efficiency, high yield, no by-products and environmental protection when herbacetin is prepared by using medical *Rhodiola* L. as raw material.

4) Polyamide used as a separation material for chromatography has better adsorption performance and separation effect on herbacetin, short cycle, good separation effect and low price. The process is simply and economically operated, easy for elution and regeneration, can be repeatedly operated, and is one of the classic methods for purifying flavonoids compounds. Compared with the silica-gel column chromatography with high dead adsorption of herbacetin, severe tailing, low recovery rate and long elution period, the polyamide column chromatography can solve the above problems effectively;

5) Reverse-phase silica-gel column chromatography for purification has good separation effect, and is easily operated and suitable for industrial production;

6) High-purity herbacetin can be obtained for providing a solid material basis for testing pharmacological activities of *Rhodiola* L. such as antioxidation, treatment of cardiovascular and cerebrovascular diseases and antitumor effect.

DETAILED DESCRIPTION OF THE PREFERRED EMBODIMENT

In order to deepen the understanding of the invention, the invention will be further described in detail in combination with embodiments which are used for explaining the invention only and do not limit the protection range of the invention.

Figure 1:
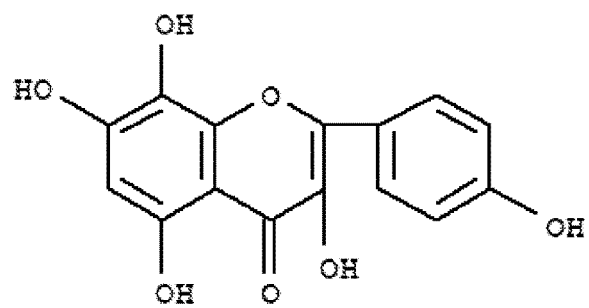
FIG. 1 is a chemical structure diagram of herbacetin.

The method for determining the chemical structure of herbacetin (as shown in FIG. 1) is as follows: samples are analyzed by using a nuclear magnetic resonance spectrometer, $^1$H-NMR (400 MHz, DMSO-$d_6$): 11.91 (1H, s, 5-OH), 10.37 (1H, s, 7-OH), 10.08 (1H, s, 4'-OH), 9.29 (1H, s, 3-OH), 8.62 (1H, s, 8-OH), 8.17 (2H, d, J=8.4 Hz, H-2',6'), 6.94 (2H, d, J=8.4 Hz, H-3',5'), 6.27 (1H, s, H-6). The above data are consistent with the nuclear magnetic data reported in the literature, the sample is identified as herbacetin.

Figure 2:
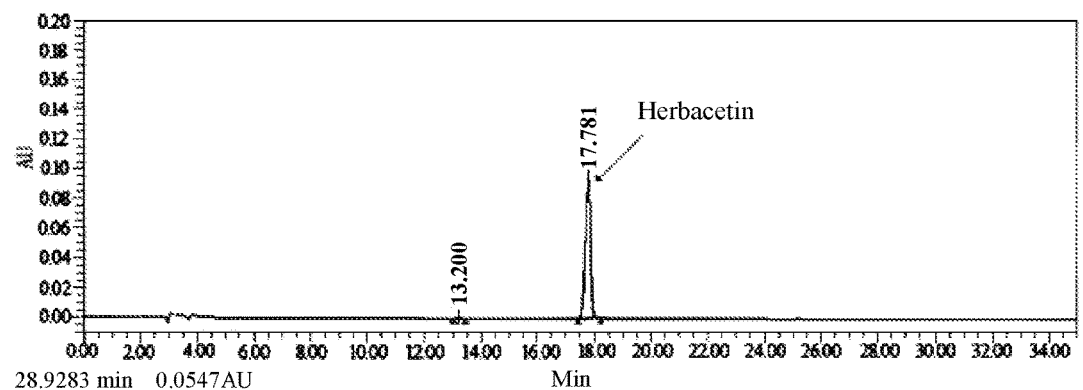
FIG. 2 is a chromatogram of pure herbacetin product.

Referring to FIG. 2, the purity testing conditions of herbacetin are as follows: the sample is tested by a high performance liquid chromatograph (HPLC) under the chromatographic conditions that the mobile phase is acetonitrile (A)-0.1% acetic acid aqueous solution (B), the gradient elution condition is [0 min, A-B (8:92); 10 min, A-B (31:69); 25 min, A-B (45:55)], the wavelength is 275 nm, Kromasil C18 column (4.6×250 mm, 5 µm) is used at the flow rate of 1.0 mL·min$^{-1}$ and with the column temperature of 35° C., and the sample shows a single symmetric peak in HPLC.

In the process of polyamide column chromatography and reverse-phase column chromatography, a thin layer chromatography (TLC) can be used to track the obtained outflow. The condition of TLC is chloroform-methanol-formic acid (12:1:1) as TLC developing solvent, inspected under ultraviolet light after being developed.

Example 1

Figure 3:
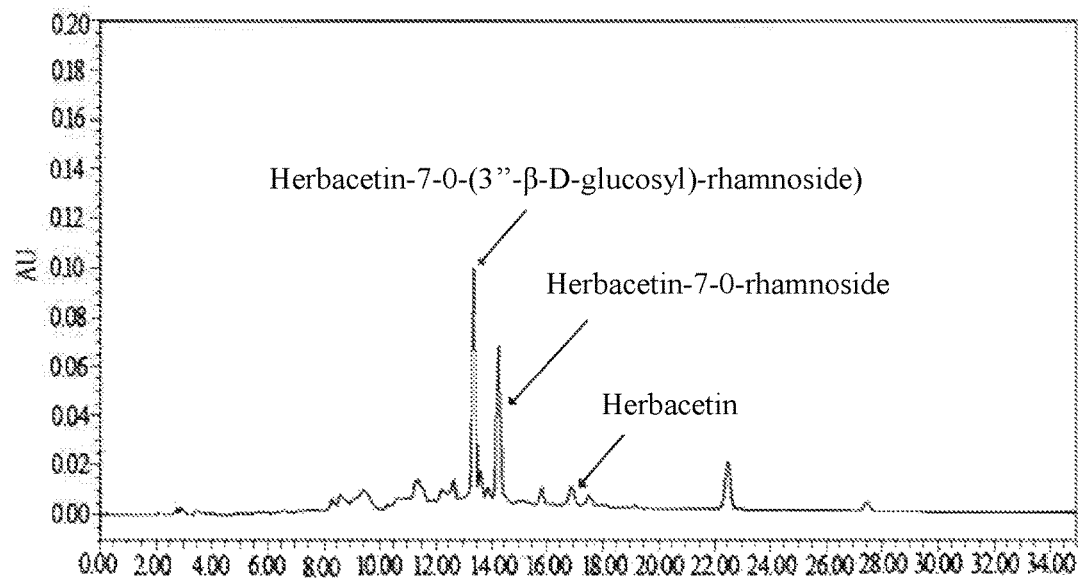
FIG. 3 is a test chromatogram of medical *Rhodiola crenulata* from Tibet before acid hydrolysis in Example 1.
Figure 4:
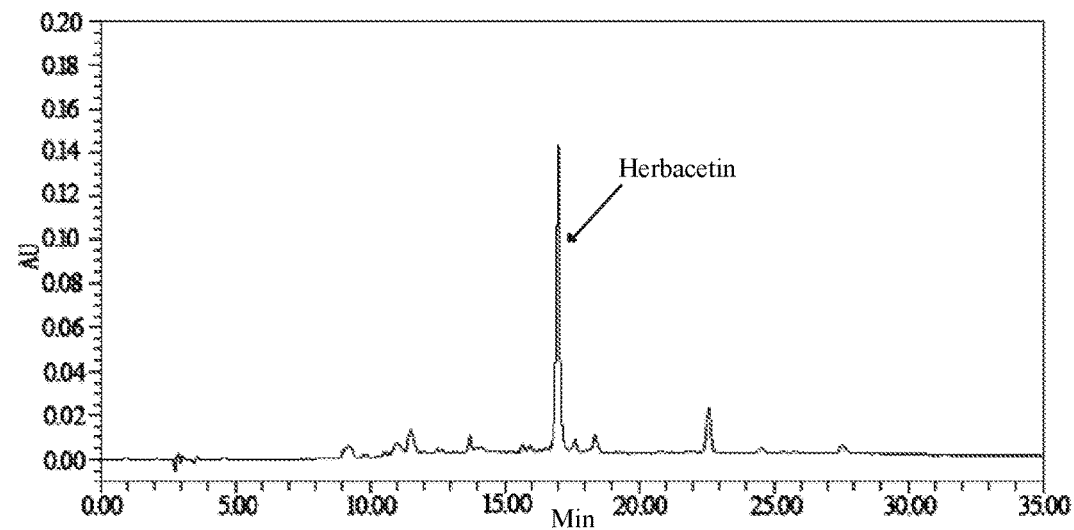
FIG. 4 is a test chromatogram of medical *Rhodiola crenulata* from Tibet after acid hydrolysis in Example 1.

Weigh 20 kg *Rhodiola crenulata* from Tibet (the content of herbacetin-7-0-rhamnoside and herbacetin-7-0-(3"-β-D- glucosyl)-rhamnoside tested by HPLC is 0.12% and 0.11% respectively. See FIG. 3 for the liquid-phase test chromatogram of medical *Rhodiola crenulata* and see FIG. 4 for the test chromatogram after acid hydrolysis), crush it to pass through a 20-mesh sieve, and heat and reflux it twice by using 10× amount of ethanol solution with the mass percentage of 70%, 1.5 h for each time. Mix and condense the solution under reduced pressure to obtain ethanol extract (the relative density is 1.072) which is then leached by using petroleum ether (60° C.-90° C.) with the same volume for 3 times. Add sulfuric acid (mass percentage of 1%) with equal volume and ethyl acetate with 2× volume of the extract to the aqueous layer after the leaching process, stir them, carry out the heating reflux for two-phase acid hydrolysis, hydrolyze them for 12 h and cool them, and then perform the leaching process for the hydrolysate with petroleum ether-ethyl acetate (1:1) (v/v) for 3 times, the ratio of the dosage of petroleum ether-ethyl acetate (1:1) (v/v) to the hydrolysate is 1:1 (v/v) at each time, and condense the organic layer under reduced pressure to obtain 831.2 g extract. The content of herbacetin in the extract is 11.38% after testing.

Example 2

Figure 5:
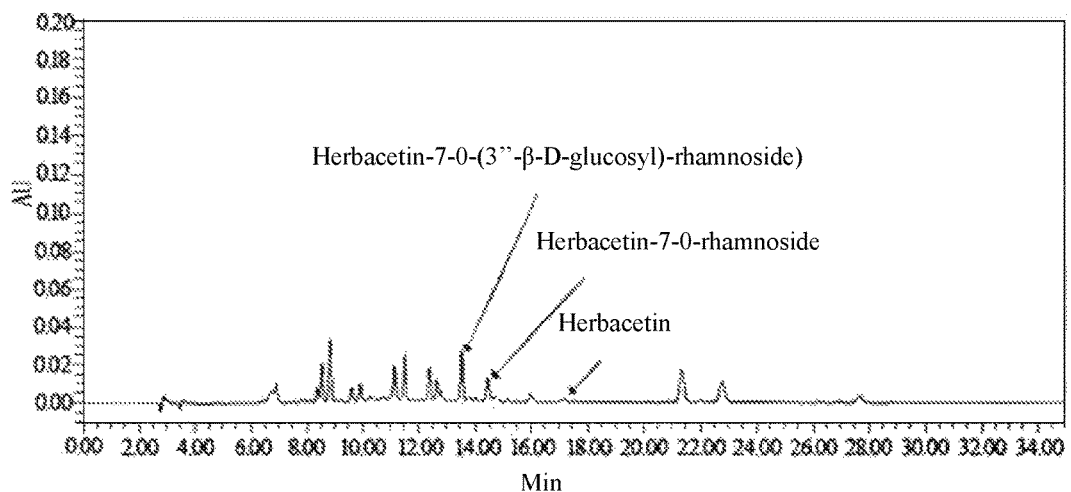
FIG. 5 is a test chromatogram of medical *Rhodiola sachalinensis* from Changbai Mountain of Jilin before acid hydrolysis in Example 2.
Figure 6:
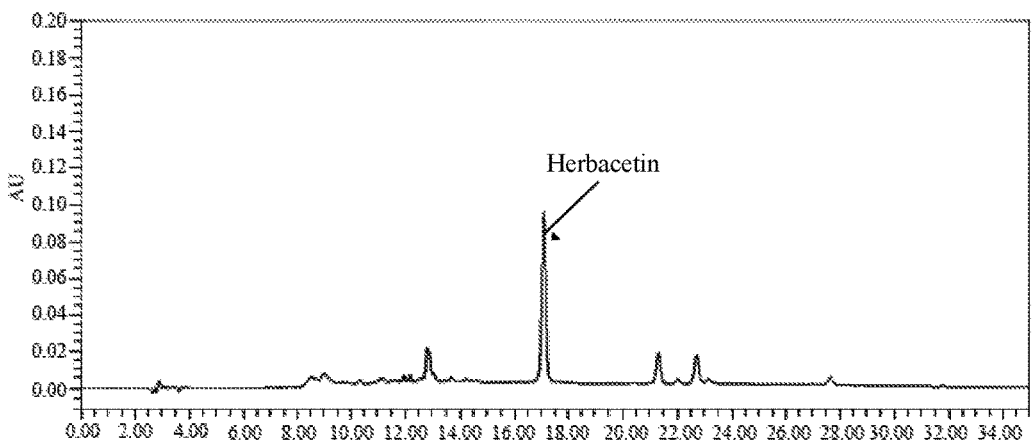
FIG. 6 is a test chromatogram of medical *Rhodiola sachalinensis* from Changbai Mountain of Jilin after acid hydrolysis in Example 2.

Weigh 80 kg *Rhodiola sachalinensis* from Changbai Mountain of Jilin (the content of herbacetin-7-0-rhamnoside and herbacetin-7-0-(3"-β-D-glucosyl)-rhamnoside tested by HPLC is 0.067% and 0.028% respectively. See FIG. 5 for the liquid-phase test chromatogram of medical *Rhodiola rosea* and see FIG. 6 for the test chromatogram after acid hydrolysis), crush it to pass through a 20-mesh sieve, and percolate it twice by using 12× amount of ethanol solution with the mass percentage of 90%. Condense percolated liquid under reduced pressure to obtain ethanol extract (the relative density is 1.136) which is then leached by using petroleum ether (60-90° C.) with the same volume for 3 times. Add hydrochloric acid (mass percentage of 5%) with equal volume to the aqueous layer first, and then add ethyl acetate with 2× volume, stir them, carry out the heating reflux for acid hydrolysis 3 h and cool them. Perform the leaching process for the hydrolysate with ethyl acetate for 3 times, the ratio of the dosage of ethyl acetate to the hydrolysate is 1:1 (v/v) at each time, and condense the organic layer under reduced pressure to obtain 1689.4 g extract. The content of herbacetin in the extract is 7.56% after testing.

Example 3

Weigh 10 kg *Rhodiola* from Lijiang, Yunnan (the content of herbacetin-7-0-rhamnoside and herbacetin-7-0-(3"-β-D-glucosyl)-rhamnoside tested by HPLC is 0.10% and 0.10% respectively), crush it to pass through a 20-mesh sieve, and perform the ultrasonic extraction three times by using 12× amount of methanol solution with the mass percentage of 90%, 1 h for each time. Mix and condense the solution under reduced pressure to obtain methanol extract (the relative density is 1.025) which is then leached by using petroleum ether (60-90° C.) with 3× volume for 3 times. Add hydrochloric acid (mass percentage of 1%) with equal volume to the aqueous layer after the leaching process, stir them, carry out the heating reflux for acid hydrolysis, hydrolyze them for 1 h and cool them. Add petroleum ether-ethyl acetate (1:1) (v/v) to the hydrolysate and perform the leaching process for 5 times, the ratio of the dosage of petroleum ether-ethyl acetate (1:1) (v/v) to the hydrolysate is 1:1 (v/v) at each time, and condense the organic layer under reduced pressure to obtain 402.7 g extract. The content of herbacetin in the extract is 10.69% after testing.

Example 4

Load 831.2 g extract in Example 1 to a non-pressurized polyamide column adsorption chromatography, the polyamide is 200-400 meshes and the column has a diameter-length ratio of 1:15, petroleum ether-ethyl acetate (1:1) (v/v) as eluted solvent, collect the outflow containing herbacetin by thin layer chromatography monitoring, and dry it through condensation under reduced pressure to obtain 167.4 g crude herbacetin product. Then perform chromatography for the crude herbacetin product through a reverse-phase DAC preparative column (200×250 mm, 10 μm), elute it by an acetonitrile-aqueous solution (containing 0.1% acetic acid) with the mass percentage of 26%, monitor by thin layer chromatography, combine target outflows, recover the solvent to dry under reduced pressure, dissolve and re-crystallize with methanol, stay overnight at 4° C., filter out crystals and dry them under reduced pressure to obtain 54.5 g herbacetin with a purity of 90.10%.

Example 5

Load 563.1 g extract in Example 2 to a non-pressurized polyamide column adsorption chromatography, the polyamide is 200-400 meshes and the column has a diameter-length ratio of 1:17, petroleum ether-ethyl acetate (1:1) (v/v) as eluted solvent, collect the outflow containing herbacetin by thin layer chromatography monitoring, and dry it through condensation under reduced pressure to obtain 80.1 g crude herbacetin product. Then perform chromatography for the crude herbacetin product through a C18 preparative column (50×250 mm, 10 μm), elute it by a methanol-aqueous solution (containing 0.1% acetic acid) with the mass percentage of 32%, monitor by layer chromatography, combine target outflows, recover the solvent to dry under reduced pressure, dissolve and re-crystallize it with methanol, stay overnight at 4° C., filter out crystals and dry them under reduced pressure to obtain 18.7 g herbacetin with a purity of 95.25%.

Example 6

Load 402.7 g extract in Example 3 to a non-pressurized polyamide column adsorption chromatography, the polyamide is 200-400 meshes and the column has a diameter-length ratio of 1:14, petroleum ether-ethyl acetate (1:1) (v/v) as eluted solvent, collect the outflow containing herbacetin by thin layer chromatography monitoring, and dry it through condensation under reduced pressure to obtain 90.2 g crude herbacetin product. Then perform chromatography for the mother liquor of herbacetin through the C18 preparative column (100×200 mm, 10 μm), elute it by an acetonitrile-aqueous solution (containing 0.1% acetic acid) with the mass percentage of 26%, monitor by thin layer chromatography, combine target outflows, recover the solvent to dry under reduced pressure, dissolve and re-crystallize it with methanol, stay overnight at 4° C., filter out crystals and dry them under reduced pressure to obtain 23.4 g herbacetin with a purity of 99.90%.

The above embodiments are only used for illustrating technical thoughts and features of the invention, and the purpose is to make a person skilled in the art know and implement the content of the invention, but not to limit the scope of protection in the invention. All equivalent changes or modifications made according to the spiritual essence of the invention shall fall within the protection scope of the invention.

The invention claimed is:
1. A method for extracting herbacetin from plants of *Rhodiola* L., comprising the following steps:
   1) performing an extracting process for the pulverized medical *Rhodiola* L. with an extracting solvent, and condensing the solution under reduced pressure to obtain an extract;
   2) performing a leaching process for the extract and performing an acid hydrolysis for the leached aqueous layer;
   3) performing a leaching process for the solution after the acid hydrolysis with an organic solvent, concentrating the organic layer under reduced pressure to obtain a herbacetin extract;
   4) treating the herbacetin extract through polyamide column chromatography, collecting the outflow containing herbacetin and drying through condensation to obtain a crude herbacetin product;
   5) treating the crude herbacetin product through reverse-phase silica-gel column chromatography, collecting the outflow containing herbacetin, drying through condensation and recrystallizing to obtain a pure herbacetin product.

2. The method for extracting herbacetin from plants of *Rhodiola* L. according to claim 1, wherein the *Rhodiola* L. in step 1) is any one of plants of *Rhodiola* L. in Crassulaceae, containing herbacetin-7-0-rhamnoside and herbacetin-7-0-(3″-β-D-glucosyl)-rhamnoside with the total content of not less than 0.08%.

3. The method for extracting herbacetin from plants of *Rhodiola* L. according to claim 1, wherein the extracting solvent in step 1) is a methanol-aqueous solution with the mass percent of 30.0%-99.9% or an ethanol-aqueous solution with the mass percent of 70.0%-90.0%.

4. The method for extracting herbacetin from plants of *Rhodiola* L. according to claim 1, wherein the extracting process in step 1) comprises any one of immersion, percolation, ultrasonic and heating reflux methods.

5. The method for extracting herbacetin from plants of *Rhodiola* L. according to claim 1, wherein the leaching process in step 2) is performed by using petroleum ether with a boiling range from 60° C. to 90° C., and the ratio of the dosage of petroleum ether to that of the extract is (1-3):1 (v/v).

6. The method for extracting herbacetin from plants of *Rhodiola* L. according to claim 1, wherein the acid hydrolysis in step 2) refers to a direct acid hydrolysis or a two-phase acid hydrolysis performed by using any one of hydrochloric acid, sulfuric acid and formic acid, with the mass percentage of 0.2%-10.0%.

7. The method for extracting herbacetin from plants of *Rhodiola* L. according to claim 6, wherein the organic phase in the two-phase acid hydrolysis comprises any one of petroleum ether-ethyl acetate (1:1) (v/v), methylbenzene and ethyl acetate.

8. The method for extracting herbacetin from plants of *Rhodiola* L. according to claim 1, wherein the heating reflux temperature is 50° C.-100° C. and the acid hydrolysis time is 0.5 h-12.0 h during the acid hydrolysis in step 2).

9. The method for extracting herbacetin from plants of *Rhodiola* L. according to claim 1, wherein the organic solvent for the leaching process in step 3) is petroleum ether-ethyl acetate (1:1) (v/v) or ethyl acetate, the ratio of the organic solvent to the solution of acid hydrolysis is (1:3):1 (v/v) each time, and the leaching process is performed for 3-5 times.

10. The method for extracting herbacetin from plants of *Rhodiola* L. according to claim 1, wherein the elution condition for polyamide column chromatography in step 4) is based on the ratio of petroleum ether to ethyl acetate (1:1) (v/v).

11. The method for extracting herbacetin from plants of *Rhodiola* L. according to claim 1, wherein the reverse-phase silica-gel column chromatography in step 5) is performed by using a C18 reverse-phase column, and the pre-packed column with an inner diameter of 50 mm or the pre-packed column with an inner diameter of 100 mm or the DAC preparative column is used as the C18 reverse-phase column.

12. The method for extracting herbacetin from plants of *Rhodiola* L. according to claim 1, wherein the eluent for reverse-phase silica-gel column chromatography in step 5) is an aqueous acetonitrile solution or an aqueous methanol solution, and the recrystallizing process is performed by using a methanol solution.

* * * * *